US012714565B2

(12) United States Patent
Arabkhani et al.

(10) Patent No.: US 12,714,565 B2
(45) Date of Patent: Aug. 25, 2026

(54) DEVICE FOR AORTIC ROOT AND VALVE VISUALIZATION AND AORTIC VALVE LEAKAGE MEASUREMENT

(71) Applicant: ACADEMISCH ZIEKENHUIS LEIDEN (H.O.D.N. LUMC), Leiden (NL)

(72) Inventors: Bardya Arabkhani, Leiden (NL); Marcus Alexander Van Barneveld, Leiden (NL); Dirk Pieter Bruin, Leiden (NL); Mark Gerard Hazekamp, Leiden (NL); Robert Johannes Menno Klautz, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 271 days.

(21) Appl. No.: 18/715,220

(22) PCT Filed: Dec. 2, 2022

(86) PCT No.: PCT/NL2022/050693

§ 371 (c)(1),
(2) Date: May 31, 2024

(87) PCT Pub. No.: WO2023/101552

PCT Pub. Date: Jun. 8, 2023

(65) Prior Publication Data

US 2025/0032259 A1 Jan. 30, 2025

(30) Foreign Application Priority Data

Dec. 2, 2021 (NL) .................................... 2029993

(51) Int. Cl.
*A61F 2/24* (2006.01)
*A61B 1/313* (2006.01)
(Continued)

(52) U.S. Cl.
CPC .......... *A61F 2/2472* (2013.01); *A61B 1/3137* (2013.01); *A61B 5/6876* (2013.01);
(Continued)

(58) Field of Classification Search
CPC .... A61F 2/2472; A61F 2/06; A61F 2240/008; A61F 2250/0069; A61B 1/3137;
(Continued)

(56) References Cited

U.S. PATENT DOCUMENTS

2017/0086964 A1 3/2017 Sperling et al.
2019/0046317 A1* 2/2019 Murad ................. A61F 2/2445
(Continued)

FOREIGN PATENT DOCUMENTS

CN 105813603 A * 7/2016 .............. A61F 2/06
EP 1943942 B1 1/2010
(Continued)

OTHER PUBLICATIONS

CN-105813603-A, English Translation (Year: 2016).*
(Continued)

*Primary Examiner* — Ryan D Walsh
(74) *Attorney, Agent, or Firm* — NIXON PEABODY LLP; Ronald I. Eisenstein; Nicole D. Kling

(57) ABSTRACT

Provided herein is a device for simultaneous intraoperative leak testing and visualisation of a heart valve seat, the device comprising an end cap configured to engage with and to sealingly close an opening of a tubular vascular graft, the end cap comprising a backing portion, a connector portion, a view port, and at least one fluid conduit element, the connector portion comprising a distal end dimensioned for placement inside of the opening, a first fastening element comprising an external thread, a second fastening element comprising an internal thread and configured to be rotated onto the first fastening element, and the external and internal
(Continued)

threads are adapted such that the first and second fastening elements are fittingly engaged with the tubular vascular graft scalingly secured therebetween by less than one rotation of the second fastening element around the outer circumference.

20 Claims, 11 Drawing Sheets

(51) Int. Cl.

| | |
|---|---|
| ***A61B 5/00*** | (2006.01) |
| ***A61B 17/12*** | (2006.01) |
| ***A61B 90/00*** | (2016.01) |
| ***A61B 90/30*** | (2016.01) |
| ***A61F 2/06*** | (2013.01) |

(52) U.S. Cl.
CPC .......... *A61B 17/1204* (2013.01); *A61B 90/30* (2016.02); *A61B 90/361* (2016.02); *A61F 2/06* (2013.01); *A61F 2240/008* (2013.01); *A61F 2250/0069* (2013.01)

(58) Field of Classification Search
CPC ... A61B 5/6876; A61B 17/1204; A61B 90/30; A61B 90/361
See application file for complete search history.

(56) References Cited

U.S. PATENT DOCUMENTS

| | | | |
|---|---|---|---|
| 2020/0060806 | A1 | 2/2020 | Dinges et al. |
| 2021/0052388 | A1 | 2/2021 | Gomez |

FOREIGN PATENT DOCUMENTS

| | | | |
|---|---|---|---|
| EP | 3400902 | B1 | 1/2020 |
| FR | 2776911 | A1 | 10/1999 |
| WO | 2018206495 | A1 | 11/2018 |
| WO | 2021151028 | A1 | 7/2021 |

OTHER PUBLICATIONS

Vahanian et al. "2021 ESC/EACTS Guidelines for the management of valvular heart disease: developed by the Task Force for the management of valvular heart disease of the European Society of Cardiology (ESC) and the European Association for Cardio-Thoracic Surgery (EACTS)." European heart journal 43.7: 561-632 (2022).

* cited by examiner

DEVICE FOR AORTIC ROOT AND VALVE VISUALIZATION AND AORTIC VALVE LEAKAGE MEASUREMENT

CROSS-REFERENCE TO RELATED APPLICATIONS

This application is a 35 U.S.C. § 371 National Phase Entry Application of International Application No. PCT/NL2022/050693 filed Dec. 2, 2022, which claims benefit under 35 U.S.C. § 119(a) of NL Application No. 2029993 filed Dec. 2, 2021, the contents of which are incorporated herein by reference in their entireties.

FIELD OF THE INVENTION

The present disclosure relates to a device and system for measuring aortic valve leakage and for visualization of the aortic valve during operation, for aortic root and/or aortic valve pathology, as well as a method of visualising an aortic root segment during a valve-sparing surgery for use therewith.

BACKGROUND

Cardiac disorders, representing the main causes of death in particular in Western societies, have a number of different causes. They can originate from structural defects inside cardiac muscle cells; heart valve defects; volume or pressure overloads of the heart, causing loss of myocardial tissue and replacement fibrosis, and systemic triggers such as hypertension, diabetes, and renal failure. Aortic valve diseases may be caused by a heart defect present at birth. They can also be caused by other conditions, including age-related changes to the heart, infections, high blood pressure, connective tissue disease or injury to the heart. The aortic valve is typically the most affected valve in the heart. This could for instance be due to degenerative calcification of the valve causing an obstructive, narrowed valve pathology, whereby no repair (only replacement) is possible.

Another pathology is dilatation or dissection of the aortic root, where the aortic valve is situated, leading to leakage of the valve during the diastolic heart cycle. Aortic valve leakage could also occur due to restriction or prolapse of the valve leaflets.

A common cause is aortic root dilatation, whereby the sinuses of the Valsalva are migrating outward, and the inter-commissural distances are expanding. Geometrically, this derangement not only increases the annular circumference, but also reduces the heart valve function and geometry until a gap may occur and the resultant increasing aortic insufficiency (leakage).

The recommended surgical therapy, according to the 2021 ESC/EACTS Guidelines for the management of valvular heart disease, for aortic aneurysms and/or leakage of the aortic valve root is the so-called "valve sparing aortic root replacement", in which the native aortic valve is spared (and/or "repaired", however the case may be) and reattached in a vascular prosthesis, further referred to herein as "vascular graft" or "graft". Usually, a dilated aortic root is resected, and the aortic valve is reimplanted within a tubular prosthesis or graft, which is reattached to the distal ascending aorta. Two similar procedures have been developed for the latter, avoiding the use of prosthetic aortic valves, and retaining the native leaflets. Compared to prosthetic valves, a valve sparing/repairing operation is associated with better hemodynamics, reduces the risk of thromboembolism and endocarditis, and eliminates the need for anticoagulation medication, thereby improving the overall quality of life of the patient. It should be noted that alternative procedures, such as biological and mechanical valve replacement, are generally associated with more valve-related events due to anticoagulant use in mechanical valves and lower durability of biological valves.

However, a disadvantage of these techniques lies in the risk of reduced valve durability due to the non-physiologic opening and closing characteristics, to incomplete restitution of normal valve configuration, and to issues of leakage at the various attachments in the heart. As the surgery is performed when the heart is arrested and void of fluids during surgery, it is very difficult to predict the postoperative final results in terms of valve geometry and competence.

In the surgery procedures in hand, the aortic valve remains either untouched, or the valve is corrected where necessary, and then affixed into a vascular graft that is implanted into the patient's heart. The vascular graft is then connected to the patient's vessels along the valve.

While these operations have greatly increased the life expectancy and life quality of patients in need thereof, to date the proper functionality and sufficiency of the valve within the graft is verified only after re-establishing the circulatory system of the patient by closing the aorta and weaning from the heart-lung machine. In case the verified function is insufficient and an additional correction is required, the additional procedure is highly cumbersome, and increases operation times, both aortic clamp and perfusion time, which is associated with higher morbidity and mortality of patients. Moreover, it reduces efficient use of the surgical facilities and the operation theatre.

The effects of leakage upon the post-operative valve transplant patient may include hemolysis, hemodynamic instability, dehiscence, or valvular dysfunction and impaired cardiac function. The assessment of leakage through the valve and proper valve operation, has thus far been performed after the surgery, and in vivo using indirect methods of analysis, such as echocardiographic colour flow Doppler ultrasound imaging and tracing, which is presently considered the gold standard. There are however disadvantages associated with the latter methods. Ultrasound colour flow Doppler imaging algorithms yield a high degree of random and systematic error when assessing a 3-dimensional structure with multidirectional flow regions; derived transvalvular pressure measurements tracing to a leakage can be inaccurate and unquantifiable; and generally, this requires the presence of a separate operator in the operation theatre.

EP3400902 discloses an aortic graft occluder that may be used for intra-operative leak testing of a partially implanted tubular aortic graft. The aortic graft occluder provides fluid access to the lumen of the graft, allowing the lumen of the graft to be filled with fluid for pressurizing the interior of the graft. This device therefor may permit to verify leak tightness of the attachment of the graft, specifically at its attachment site, and to verify leak tightness across the aortic valve. The document further proposes to apply, simultaneously, imaging of the valve by a transesophageal ultrasound technique, to ascertain the proper functionality of the valve during the surgery.

A disadvantage of the device and process disclosed in EP3400902 resides in the need to operate two separate processes to confirm absence of leaks in the graft attachment, the connection to the graft and the generation of the liquid pressure in the aortic root and, separately, transesophageal ultrasound visualisation of the aortic root seat. This requires at least an additional operator in the surgical theatre, and may not be suitable for operations where space is restricted.

Hence, the methods used to date involving indirect measurements of leakage from regions of the valve structure do not provide a truly quantifiable or absolute measurement of leakage. While existing methods of valve testing apply only to the evaluation of the valve leaflet function, there is an unmet and pressing need for a novel apparatus and in vivo method for evaluation of the integrity of valve fixation and functionality and the measurement of leakage. The present invention aims at overcoming these risks and problems.

SUMMARY OF THE INVENTION

The present invention relates to a device for the simultaneous intraoperative leak testing and visualisation of a heart valve seat or functioning during a procedure, including but not limited to, any one or more of: valve-sparing aortic root replacement, aortic valve repair, supracoronary aortic root replacement, procedures in which replacement of the distal ascending aorta which could lead to geometrical changes of the aortic root, thereby causing aortic valve leakage, a pulmonary autograft operation (i.e. the Ross procedure, mainly in congenital valve disease), any other operation on the aortic root which may lead to changes in root geometry and hence valve function, in procedures where the aortic root is replaced by a vascular graft, in procedures where the native ascending aorta has to be addressed, and in operations on the aortic valve pursuing to repair the valve, even without replacement of the root.

A device for simultaneous intraoperative leak testing and visualisation of a heart valve seat or functioning during any operation leading to valve incompetence is provided comprising an end cap configured to engage with and to sealingly close an opening of a tubular vascular graft or native aorta, the end cap comprising an interior, an exterior, a backing portion, a connector portion arranged adjacent to the backing portion, a view port arranged in the backing portion and protruding along a central axis from the backing portion through at least a part of the connector portion, and at least one fluid conduit element adapted to provide fluid communication between the interior and the exterior, the connector portion comprising a body with opposing proximal and distal ends, the distal end dimensioned for placement inside of the opening of the tubular vascular graft, a first fastening element provided on an outer circumference of at least the distal end of the body of the connector portion, the first fastening element comprising an external thread, a second fastening element comprising an internal thread, the second fastening element configured to be rotated onto the first fastening element for fitting engagement therewith, and wherein the external and internal threads each comprise a respective thread pitch, the respective thread pitches adapted such that the first and the second fastening elements are fittingly engaged with the tubular vascular graft sealingly secured therebetween by less than one rotation of the second fastening element around the outer circumference, and whereby the fitting engagement provides a fluid and pressure tight seal around the tubular vascular graft.

Having a second fastening element that fittingly engages with the first fastening element, with the tubular vascular graft secured therebetween, after less than one full rotation of the second fastening element around the outer circumference of the first fastening element is particularly desirable because it enables the device to be sealingly secured in place with the tubular vascular graft with relative ease and speed. In terms of ease of use, it is possible with this configuration to manipulate the second fastening element single-handedly. Also, the partial rotation of the second fastening element around the outer circumference of the first fastening element to secure the device in place can be considered to reduce an amount of force imparted on the tubular vascular graft, which is secured between the first and second fastening element. Moreover, being able to quickly secure the tubular vascular graft in place contributes to reducing the overall duration of the procedure, which by extension, can have an appreciable effect on the patient's well-being during and after the procedure.

In an embodiment, the connector portion may comprise an outer flange forming a member extending in a longitudinal direction along a longitudinal axis of the end cap. The outer flange is configured to contact an interior surface of the distal end of the tubular vascular graft.

The connector portion may take a number of different shapes. Some non-limiting examples of shapes that the connector portion may have in embodiments of the present device may include those formed as a hollow cylindrical, conical, frustoconical, stepped conical, stepped cylindrical, or tapered body. Further, the distal end of the connector portion, which carries the taper engages with an interior of the distal end of the tubular vascular graft.

The shape of the connector body may also be dimensioned to engage with different grafts having different inner diameters. This ensures flexibility during a procedure since the end cap, and particularly the connector portion thereof, can advantageously be used in combination with any one of the differently sized tubular vascular grafts and the corresponding respectively sized second fastening element.

In an embodiment, the device may have an axially symmetric or essentially axially symmetric form. It is to be understood, however, that the form of the device is not particularly limited, and it is contemplated that the form may be readily adapted by one of ordinary skill in the field.

The external thread may comprise a rounded edge. It is further preferable that the external thread does not comprise a sharp edge since it is meant to directly interface with a portion of the tubular vascular graft. Rounded edges are desirable to avoid damage, such as a puncture, tear, or the like, to the tubular vascular graft.

The backing portion and the connector portion may be formed integrally in an embodiment. Alternatively, the backing portion and the connector portion may be formed from two elements that are configured to fit and mutually engage with one another to form a double walled chamber.

The backing portion and connector portion may also form or be shaped to form a chamber in which air bubbles are entrapped and outside of view of the view port.

In an embodiment, the view port may comprise an insertion opening which is sized to receive a visualisation tool for visualisation of the heart valve seat or heart valve function under a fluid pressure differential. The insertion opening is oriented along in a longitudinal direction along a longitudinal axis (y) of the end cap.

The view port may also be formed as a tapered conical protrusion in the backing portion extending toward the connector portion. This enables the angle of the visualisation tool relative to the viewing position, i.e. through the view port, to be adjusted while the device is maintained in position. Moreover, this configuration is advantageous because it facilitates ease of use of the device during a procedure, and particularly, it makes it possible to adjust the device using only one hand.

In a non-limiting embodiment, the insertion opening, like the view port, may be provided in or take the form of a tapered or conical shape, the distal end of which is relatively wide. A relatively wide distal end means that the visualisation tool has appropriate space to acquire views of the operation site, and more preferably the valve(s), from a plurality of sides and/or angles. To this end, having a relatively wide distal end, with which the visualisation tool interfaces, is desirable to maximize the range of available space in the insertion opening in which the visualisation tool can be manoeuvred and facilitates the aforementioned acquisition of a plurality of views and/or angles of the operation site.

Additionally, in terms of orientation, the view port is preferably spaced in an axial direction from the backing portion toward a lumen of the tubular vascular graft.

The view port may further comprise an inner engagements mean for the visualisation tool. This is desirable again to facilitate ease of use of the device during a procedure, particularly so that the device can be manipulated with just one hand. In an embodiment, the inner engagement means may extend centrally through the device in a longitudinal direction along a longitudinal axis (y) of the device and terminating at the backing portion.

In an embodiment, the view port may comprise a transparent window element. This transparent window element may serve as a closure abutment to sealingly close the view port towards the lumen of the tubular vascular graft.

Further, the view port is adapted to be filled with a fluid into which a visualisation tool, for example, an endoscopic camera, is immersed. Having the view port fluid filled with fluid so that the visualisation tool is capable of being at least partially, if not substantially, or fully immersed in the fluid is particularly advantageous for improving the quality of the visualisation. More specifically, having the visualisation tool immersed in a fluid facilitates to reduce the refraction of the light and image visible through use of the tool. This therefore provides a higher quality of imaging at the surgical site.

The visualisation tool may be embodied in a number of forms and is not particularly limited to a specific device or tool. It is contemplated that the skilled person can readily select and substitute any visualisation tool, particularly those known in the field or otherwise desirable relative to the procedure being performed. In an embodiment, the visualisation tool is preferably an endoscopic camera. In another non-limiting embodiment, the visualisation tool may comprise any one or more of an endoscopic camera, an echoscope, an echoscopic camera, and a probe.

Further, the view port may also comprise a seal. The seal can serve to engage with one or more of a visualisation tool and an illumination tool. Preferred exemplary seals may include, but are not limited to, those such as a sheath or an o-ring. However, it is to be understood that the skilled person can readily select and substitute any alternative seals or sealing elements.

In an embodiment, the device may further comprise a light source. The provision of a light source may be advantageous for improving visualisation of the operation site. It is contemplated that the light source may be provided as an add-on to the device or it may be built-in, i.e. integrated directly into the device itself. More specifically, the light source may be built-in or integrated into the end cap of the device. In one non-limiting embodiment, the light source may be integrated into the connector portion in a top end of the end cap along its longitudinal axis (y). For reference, the top end is the portion of the device that is opposite, in the longitudinal direction, to the abutment. Having the light source arranged in the top end of the device enables the light to be transferred throughout the device, especially in embodiments in which the device comprises a transparent material. The transparent material acts as a light guide and/or a diffusor of the light source. Alternatively, the light source may be integrated into the backing portion in a bottom end of the end cap along its longitudinal axis (y). By having the light source arranged in the bottom end portion, unwanted reflections inside of the device can be minimized, if not avoided entirely.

The material(s) from which the device is formed is not particularly limited. However, it is preferable that the device at least comprises a transparent material. Exemplary materials may include polymers, including but are not limited to, polycarbonate and polymethylmethacrylate (PMMA), combinations of polymers, or even metals.

In a preferred embodiment, the device is formed in one or more transparent or essentially transparent polymeric parts. The transparent polymeric parts may further be essentially uniform radiation transparent parts. While the formation method is not particularly limited, such parts may be advantageously prepared by injection moulding. Alternative methods for forming the parts may also include, but are not limited to, additive printing, cutting, or machining the same.

The device comprises at least one fluid conduit element. This fluid conduit element is preferably arranged in fluid communication with the lumen of the tubular vascular graft. In a non-limiting embodiment, the at least one fluid conduit element comprises a standardized, pressure-proof fluid connector. In a preferred, but not limiting embodiment, the standardized, pressure-proof fluid connector is a Luer connector. The terms 'Luer connector' or 'Luer type connector' may refer to either a Luer lock connector or a Luer slip connector (i.e., a Luer lock without bayonet), if not otherwise explicitly specified.

The connector is preferably adapted to sealingly close a feed line. The feed line may comprise a corresponding connector. The standardized, pressure-proof fluid connector may be any type of connector, and is preferably a Luer type connector, such as a Luer lock connector or a Luer slip type connector. Additionally or alternatively, the connector may be any connector that allows a sealed transmission of fluid in a range from 0 bar to approximately 0.6 bar.

Additionally, the at least one fluid conduit element may be shaped such that the fluid entry point is above a pocket formed directly above the entry point in the back surface. This configuration allows air bubbles trapped in the device after pressurizing to collate in the chamber, which in turn, makes it possible to reduce, if not all together avoid, obstruction(s) in view of or through the view port by the entrapped air bubbles.

Obstruction(s) in view of or through the view port caused by entrapped air bubbles can be further mitigated still through the use of a hydrophilic material, either to form at least the portion of the device (e.g., the view port) that is to come into contact with the introduced fluid, or in the form of a coating on one or more of the surface(s) of the device that is/are to come into contact with the introduced fluid.

While a single fluid conduit may suffice to remove air and fill the lumen with fluid, the device may nevertheless further comprise one or more further fluid conduits. Each further fluid conduit preferably comprises a standardized, pressure-proof fluid connector. In an embodiment, the further fluid conduits may be Luer connectors for convenient connection to a heart-lung machine.

In a non-limiting embodiment, the at least one fluid conduit element, and preferably, all fluid conduit elements comprise a standardized, pressure-proof fluid connector, such as a Luer connector. Moreover, the conduits and connectors may be arranged in any number of configurations. Some such exemplary arrangements include, but are not limited to, being opposite to one another, being at any given angle relative to each other, being adjacent to each other, or being in parallel.

Additionally, the device may be shaped and/or formed to provide a pocket in which entrapped air bubbles may be taken up and collated outside of view in the direction of the view port.

The end cap may comprise an inner wall and an outer wall and having an interior space therebetween. The interior space is advantageously adapted to trap air bubbles introduced into the device during pressurization of the same with fluid outside of view of the view port. This assists to improve visualization of the operation site.

Additionally or alternatively, the pocket in which entrapped air bubbles may be taken up may be provided as double walled backing and connection portions of the device. Again, this structure provides a dedicated bubble space above the view port abutment, thereby allowing to air bubbles entrapped in the device during or following introducing of a fluid into the device to pressurize the tubular vascular graft to collate in this dedicated chamber; and by extension, it is possible to remediate, if not all together avoid, obstruction(s) of the visualisation by the entrapped bubbles.

In an embodiment, the second fastening element may comprise a circular fastening body. This circular fastening body preferably has an inner circumference or an internal thread that is complementary to the external thread on the outer circumference of the connector portion of the device. The complementary threads permit the first and second fastening elements to be sealingly and removably secured around the distal end of the tubular vascular graft. In this sense, the tubular vascular graft is temporarily secured between the first and second fastening elements.

Further, in a non-limiting embodiment, the circular fastening body is preferably a screw nut. This screw nut may have an inner diameter sized to correspond to a diameter of a respective tubular vascular graft. In another non-limiting embodiment, when the circular fastening body is a provided in the form of a screw nut, an inner surface thereof may have a shape that is parallel to the axial direction of the device or it may have a frustoconical shape which is complementary to either or both of the shape of the body and an external thread thereon.

It is also contemplated, in certain embodiments, that the second fastening element may be coloured coded according to the different diameters of the tubular vascular graft. Colour coding the second fastening elements with the corresponding tubular vascular graft is desirable as it reduces, if not eliminates, the number of instances for misalignment between non-corresponding second fastening elements and the respectively sized tubular vascular grafts to occur. This can also have the advantage of ease of use, since the paired second fastening elements and respectively sized tubular vascular grafts are readily, visually identifiable. By extension, this may also assist to further reduce the amount of time expended, e.g. by trying to properly match or align a tubular vascular graft and fastener, during a procedure.

In another aspect of the present disclosure, a system for simultaneous intraoperative leak testing and visualisation of a heart valve seat or functioning during a valve-sparing aortic root replacement, aortic valve repair, supracoronary ascending aortic replacement, pulmonary autograft, or any other operation involving valve incompetence is provided comprising a device as described herein, a plurality of differently sized tubular vascular grafts, and a plurality of differently sized second fastening elements, each second fastening element corresponding with a respectively sized tubular vascular graft and configured to be rotated onto the first fastening element for fitting engagement therewith, wherein each differently sized tubular vascular graft is sealingly securable between the first fastening element and the respectively sized second fastening element by less than one rotation of the respectively sized second fastening element around the outer circumference of the first fastening element.

In an embodiment, the system may further comprise a fluid reservoir. The fluid reservoir preferably comprises a means to measure at least one of the volume of fluid flow over time and the pressure applied.

Additionally, the fluid reservoir may comprise a metered pump unit. Such a metered pump unit is preferably part of heart-lung machine. Moreover, the heart-lung machine preferable further comprises a flow meter.

In a further aspect of the present disclosure, a method for visualising an aortic root segment of an ascending aorta in a patient during a valve-sparing surgery using a device as described herein or a system as described herein is provided comprising the steps of: (a) providing a tubular vascular graft corresponding in size to a diameter of an aortic valve-to-be-spared or an aortic root, the tubular vascular graft having opposing proximal and distal ends and a lumen; (b) attaching the proximal end of the tubular vascular graft to the aortic valve-to-be-spared using one or more of a hook, a barb, and adhesive material, a staple, and a suture; (c) sealingly attaching the device to the distal end of the tubular vascular graft; (d) connecting the device to a fluid reservoir, preferably a metered pump unit; (e) filling the lumen with a fluid to test relative fluid-tightness of the tubular vascular graft and/or to measure the fluid flow over time; and (f) inserting a visualisation tool into the interior of the end cap to visualise the aortic heart valve seat under fluid pressure.

The method may further comprise the steps of: (g) removing the device, and (h) attaching the distal end of the tubular vascular graft to the ascending aorta, when the aortic root segment has a predefined level of valve competency against fluid leakage; or when the aortic root segment does not have the predefined level of valve competency against fluid leakage, additionally correcting the aortic root attachment or aortic valve seat, and repeating steps (a) to (f). The predefined level of valve competency may herein refer to an accepted grade of leakage in echocardiography, which is typically understood as grade 1 or less aortic valve insufficiency.

In an embodiment, a leakage per unit of time may be determined and associated with a different grade of leakage under use.

Further, the fluid introduced into the lumen may be an autologous plasma or a physiological salt solution. It may also be preferred for the fluid to be provided using a heart-lung machine measuring volume of fluid flow over time. However, it is contemplated that other fluid(s), where desirable for a particular application (e.g., blood or similar during an echoscopic application), may also be readily substituted by a person of skill in the field.

The method may comprise a step of comparing pressure variation and visual observation(s) of the valve operation with the results of an echoscopy.

The method may comprise an optional step of attaching one or more coronary arteries to the tubular vascular graft.

Finally, the method may also comprise filing the view port with a liquid, such as saline solution. If the port is filled with liquid, this advantageously facilitates imaging formation by the visualisation tool. More specifically, the addition of a fluid can serve, for example, to prevent or reduce reflection(s) due to refraction index differences with the transparent material, and particularly at the base of the view port where the visualisation tool may come into contact with the abutment, and the fluid filled lumen of the graft. Advantageously, the visualisation tool may be partially or fully submerged in the recess that is filled with fluid, for reflection-less illumination by the visualisation tool, in particular, if a light source is present, on the device, on the visualisation tool, or otherwise. One additional advantage is that the visualisation tool does not directly contact with the graft lumen and heart valve, thereby reducing the opportunity for transmission of pathogens from the tool to the graft.

BRIEF DESCRIPTION OF THE DRAWINGS

The present invention will be discussed in more detail below, with reference to the attached drawings, in which.

DETAILED DESCRIPTION

Figure 1A:
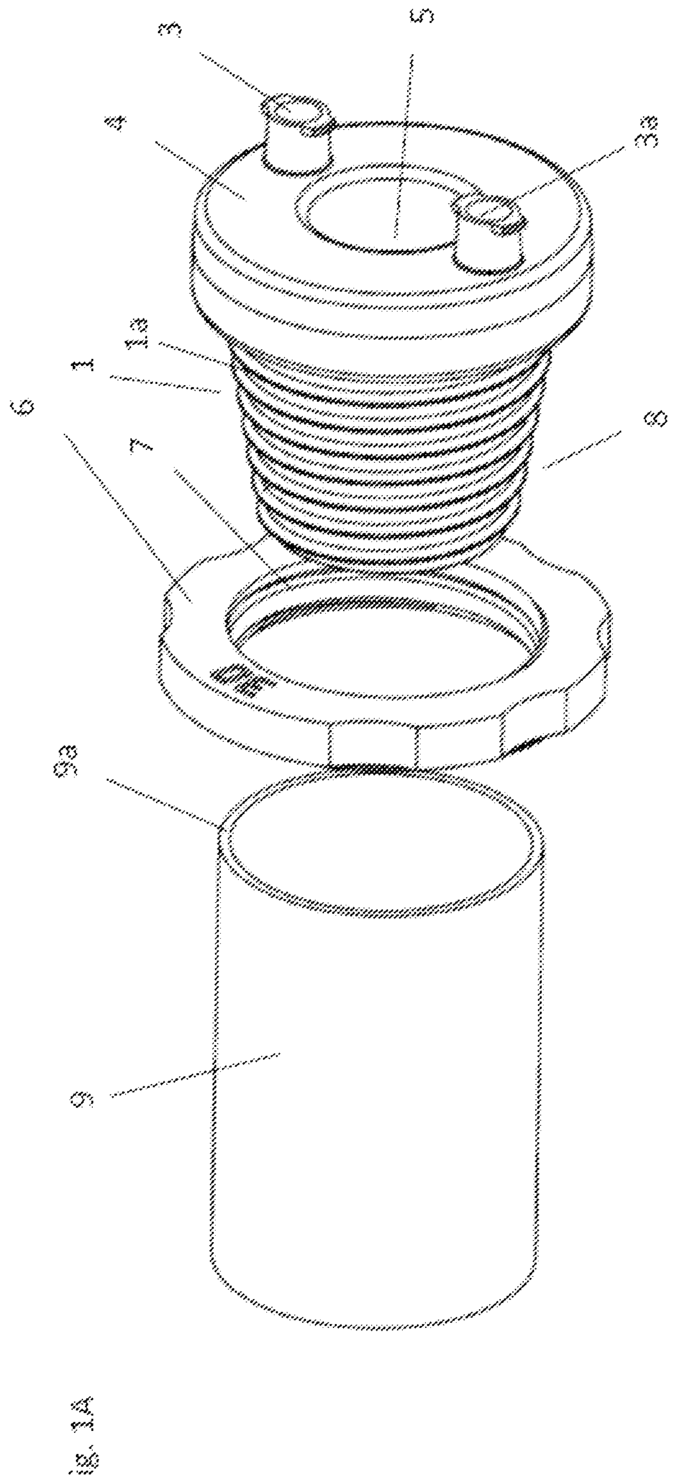
FIG. 1A shows an exploded perspective view of an exemplary double walled device.

Throughout the present application, the terms proximal and distal are used for identifying locations along a device and/or a pathway from the point of view of a user performing the surgery and/or using an embodiment of the device or system for other purposes. That is to say that something proximal is generally relatively closer to a user than something distal, unless expressly indicated otherwise. For example, the present device has opposing proximal and distal ends in a longitudinal direction along a longitudinal axis, and the distal end is the one which is relatively closer to or attached to the tubular vascular graft. This may differ from other publications relating to vessels where the terms proximal and distal are used referring to the location with respect to the heart. Moreover, as for the tubular vascular graft, which also has opposing proximal and distal ends, the proximal end is generally understood herein to refer to the portion of the graft arranged or attached closest to the heart, whereas the distal end is arranged away from the heart (i.e., toward the aortic arch).

The present device may be advantageously employed in valve-sparing root replacement procedures where a valve is reattached into a vascular graft. In this case, the graft would start from the left ventricle, at the precise location were the native aortic root was situated, which is resected. The distal part of the graft is then attached to the present device, preferably leaving sufficient distance, for instance from 1 to 3 cm, between the device and the heart valve in order to be able to visualize the heart valve.

Moreover, the present device may be advantageously used in any patient with an indication for aortic root replacement and/or aortic valve repair, due to dilatation (aneurysm) or dissection of the aortic root, or leakage of the aortic valve due to any valve pathology. Such procedures include the valve-sparing aortic root replacement, in particular the remodelling and reimplantation technique; supracoronary ascending aorta replacement; pulmonary autograft, also referred to as the “Ross procedure”, and its associated procedures, e.g. wrapped Ross technique, cylinder inclusion technique; and/or the Personalised External Aortic Root Support (PEARS) procedure or aortic valve repair. The techniques of valve sparing root replacement are constantly modified and improved. Nevertheless, these techniques still lack a possibility of verifying the correct fit and functionality of the heart valve; in particular leak tightness of the heart valve under operation; the leak tightness of one or more sutures of the graft to the one or more vessels, and the closure and opening of the leaflets of the heart valve. With the currently established technique, the medical personnel has to re-establish the circulatory system before the being actually able to verify the success of the surgery, i.e. to verify that the valve is properly working and/or that all connections at the suture sites are leak proof.

Consequently, if a leak occurs and/or the aortic valve does not work properly, another surgical correction has to be performed. This often includes cross clamping the distal aorta once more, in order to arrest the heart once more, additional manipulation of the valve leaflets, e.g. by placing sutures on leaflets or hanging the commissures lower or higher, or closing fenestrations, and the like, in order to create valve competence, modifying or replacing the aortic valve, re-establishing the patient’s circulatory system to verify the success of the surgery. This is obviously stressful and potentially harmful for the patient and adds additional risks to the surgical procedure.

To date, only after re-establishing the circulatory system of the patient by means of closing the aorta and declamping it, and weaning from heart-lung machine, may the proper functionality of the valve and the graft be verified for leakage and heart valve function, which is highly cumbersome.

The present device may also be employed in the case of a dilated ascending aorta resection, where it may be inserted just above the aortic root, whereby the ascending aorta is resected. This may advantageously include the whole aortic arch, depending on the extent of the dilatation, or part thereof. Here, the device is preferably attached to the native aorta, again just above the root, and pressurization and visualization may be performed in the same manner. If a native vascular tissue is employed (as in case, for example, of a supracoronary ascending aorta replacement), however, it is preferable that the device be sealingly attached to the native tissue with a suture or a so-called cable binder, or “snugger”. The native aorta is more pliable than a graft and should, therefore, seal more easily, though it is possible that it could also be damaged upon pressure and torque induced, for example, with a nut.

The aortic valve comprises flaps, referred to as leaflets herein, which open and close once during each heartbeat. Sometimes the valves will not open or close properly, disrupting the blood flow through the heart and potentially impairing the ability to pump blood. In aortic valve diseases, the aortic valve between the lower left heart chamber, the left ventricle, and the aorta, the main artery that delivers blood from the heart to the body, does not work properly. It may not be closing properly, which causes blood to leak backward to the left ventricle in a so-called regurgitation, or the valve may be narrowed, thus a stenosis.

The left atrium acts in a capacitor function receiving blood from the lungs via the pulmonary veins throughout the cardiac cycle. The left ventricle fills during diastole by receiving blood from the left atrium as the mitral valve opens, and then during systole, the mitral valve closes and permits forward ejection of the blood from the left ventricle into the ascending aorta.

The aortic valve is located between the left ventricle and aorta, and functions under normal conditions to allow unimpeded blood flow out of the ventricle and into the aorta during systole. During diastole, the aortic valve closes and prevents regurgitation backward into the left ventricle.

The local geometry of the aortic valve hence plays an important role in its performance.

The term "leakage" is defined herein as the flow of blood from one side of the valve to the other, while the valve is closed, through regions other than through the orifice of the valve, e.g. through and alongside the valve leaflets.

The present device thus facilitates visualisation of the heart valve seat and operation. The present device also enables pressure to be simultaneously tested when used in a valve-sparing root replacement.

The present device may also be used in other surgical techniques, such as intra-operative leak testing of other prosthetic grafts, or native aorta in case of supracoronary ascending replacement, such as in the so-called the Ross procedure.

Further, the present device may be used to sealingly close a partially implanted graft at its non-attached distal end, while the proximal end of the graft has already been connected to the patient's vessel and/or heart. Simultaneously, the device provides fluid access to the lumen of the graft. Via this access route, the lumen of the graft can be filled with fluid, whether gas or liquid, such as a saline solution. By filling the lumen of the graft with fluid, preferably a liquid, and preferably by thereby pressurizing the interior of the graft, the leak tightness of the prosthesis, the correct seat and operation of the heart valve, specifically the shape and overlay of the heart valve's leaflets, and less frequently, its sutures to tissue, can all be advantageously visualised. Moreover, it is also possible to simulate a diastolic blood pressure across the aortic valve during the procedure.

The present device is preferably used with a tubular vascular graft (e.g., prosthesis) defined by a distal end and a proximal end, relative to the perspective of the user, not to the heart and a lumen connecting the proximal end of the graft with a distal end of the device. The proximal end of the graft is ultimately intended to be connected to a patient's blood vessel, while the distal end of the graft is intended to be connected to the aortic root, where the aortic valve is implanted.

The present device advantageously enables the lumen to be filled with a fluid, e.g. a physiological saline solution or blood. By filling the lumen of the graft with fluid and preferably by thereby pressurizing the interior of the graft, the leak tightness of the graft, specifically the position, geometry and closure of the valve leaflets, may be verified. Additionally or alternatively, the graft may be used to pressurize the interior of the lumen provided by the valve, the graft and the device, to simulate a diastolic blood pressure across the aortic valve. By simultaneously imaging the valve, e.g. with a camera device or an endoscope comprising a camera positioned in the view port of the device, proper functionality of the valve may be verified during the surgery.

When filling the lumen of the graft with a fluid, excess fluid and/or gas (e.g., air) may exit the prosthesis via a second pathway. A discharge line is therefore preferably connected to the fluid conduit, preferably by means of a second connector and a corresponding connector to the discharge line. This may help to direct gas and fluid exiting the body to a safe location with respect to the patient's body for discharge or release therefrom. The fluid flow may be regulated by any suitable means. Preferably, a plug, a stop cock or cap adapted for sealingly closing the latter pathway is provided, thus inhibiting any flow through the latter pathway.

For example, the cap may comprise a thread that corresponds to a thread of the second pathway and/or the second connector, thus providing a sealingly closing connection of the cap with the second pathway. More preferably, a discharge line with a control valve is sealingly connected to the second pathway, preferably via the second connector. The control valve may be manually or automatically controllable to open and/or close the discharge line and thus the second pathway. Any suitable valve may be contemplated, e.g. any system that securely seals the second pathway in a pressure range of from 0 bar to 1.0 bar, preferably of from 0.05 bar or 0.1 bar to approximately 0.6 bar, such as a 1-way stopcock or a 2-way stopcock. Preferred connectors are Luer type connectors or central venous catheter clips.

The device may advantageously comprise a valve configured for sealingly closing the opening of the distal end of the vascular graft, such as for instance an aortic prosthesis. Common aortic prostheses are available with nominal various diameters, typically in standardised sizes such as 26 mm, 28 mm, 30 mm or 32 mm diameter, and smaller diameters for children. The varying diametrical size of the device is therefore tapered and/or circumference is advantageously selected to allow connection to aortic tubular prosthesis having different inner diameters. Preferably, the taper or circumference is selected to allow connection to aortic tubular prosthesis having different inner diameters.

The device may be, for example, configured to fit within a tapered opening in the implant, by having a lateral surface that is circular or oval in cross-section, and preferably configured to fit within a similarly configured opening in the connector portion or a combination thereof. Those ordinarily skilled in the art will be familiar with various types of engagement mechanisms that could be used to secure the attachment to the graft, including, for example various internal or external anti-rotational surfaces, tapered surfaces, lobed channels, or any combinations thereof.

Advantageously, the device may comprise a hollow, tapered, frustoconical base body with at least one external thread and a view port pointing axially in the direction of the heart. The body may be sealingly secured to the distal end of the tubular vascular graft with a second fastening element, which may be centrally fastened around an outer circumference of the body. One non-limiting example of a second fastening element is a clamping nut having an internal thread which corresponds with an external thread on the outer circumference of the body.

Here, the second fastening element is first slid over the distal end of the graft, then slid over the distal end of tapered body together with the graft (9). When the second fastening element is rotated, it moves through rotation against the body in the axial direction such that the inner core of the second fastening element moves radially, thereby sealingly securing the distal end of the graft between the body and the second fastening element. As such, the connector portion of the device acts as a male fitting for connection to the graft, which is in its turn squeezed in between the connector portion and the second fastening element. While the first and second fastening elements each comprise a respective thread, it is contemplated that other fastening mechanisms, such as external grooves or protrusions formed on either or both fastening elements can be readily substituted by the skilled person.

It is contemplated that the device use an alternative means of fixation, such a snugger usually employed in surgery, to secure the vascular graft. However, such closures, which may place torsion onto the graft and could potentially be translated towards the new sutures and heart valve tissue, are preferably avoided.

Turning now to the figures, FIG. 1A shows an embodiment of an exemplary device (1). The device comprises connector portion (4) having, in this example, a frustoconical shape. The connector portion also comprises a first fastening element (8) on an exterior surface and provided along an outer circumference. The first fastening element comprises an external thread (1*a*). The device includes a pair of fluid conduit elements (3, 3*a*) arranged on opposing ends of the diameter of the connector portion (4), and a view port (5) that is centrally located in a backing portion. The device further includes a second fastening element (6). The second fastening element is shown in the form of a fastening nut, which has an internal thread (7). In operation, the distal end of the connector portion will be inserted into the distal end (9*a*) of the tubular vascular graft (9). Thereafter, and with the tubular vascular graft arranged in between the first and second fastening element, the second fastening element is rotated around the outer circumference of the connector portion to sealingly secure the vascular graft between the first and second fastening elements.

In a preferred embodiment, the second fastening element is adapted to rotate less than one revolution, for example by 180° or any other angle less than 360°, around the outer circumference of the connector portion. The conus angle and the external thread pitch may, therefore, be chosen accordingly, i.e. such that the second fastening element can only rotate for half a turn after assembly when sliding it over graft and conus or frustum. This arrangement is particularly desirable for reducing or minimizing torsion imparted onto the graft.

In a non-limiting embodiment, the device (1) may have as a unitary structure. However, it is also contemplated that the device can alternatively be formed from a plurality of individual parts. Along a longitudinal axis (y), the device has a top end and a bottom end. The bottom end is preferably closed at by a base. At the top end, the device comprises the view port, which is preferably formed as recess extending centrally in the longitudinal direction from the backing portion through the body and into the connector portion. The recess may further serve as an inner engagement means for a visualisation tool. In this configuration, the recess ends at an abutment (5*a*). The abutment has a transparent window. The transparent window may be embedded in the abutment, or in the alternative, the transparent window may be formed integrally in the body, preferably opposite to the base. Further, the visualisation tool may be positioned up against (i.e. in direct contact with) the abutment.

The view port is configured to receive a visualisation tool. In this sense, the view port is preferably shaped to receive the visualisation tool, which in some embodiments, may including functionality for illumination. It is preferable that the view port enables the visualisation tool to be freely positioned in the recess up until it contacts the transparent window at the base. The view port may further comprise or serve as an inner engagement means (not shown) for the visualisation tool, which during operation, is preferably submerged in a fluid (not shown), to facilitate visual inspection of the underlying operation area.

The shape of the view port is not particularly limited. In one embodiment, the view port is preferably frustoconical, which is advantageous to facilitate adjustment of the visualisation tool. With the frustoconical shape, it is possible to move the visualisation tool, including its angle of orientation relative to the viewing position single-handedly and with relative ease. Further, the abutment at the base of the view port is preferably, generally flat or flat. However, it is contemplated that the shape of the view port may be adjusted, as desired, by one or ordinary skill such that it is angled or otherwise not generally flat.

Alternatively, the shape of the connector portion may be rounded, radiused, tapered, or generally frustoconical.

Figure 1B:
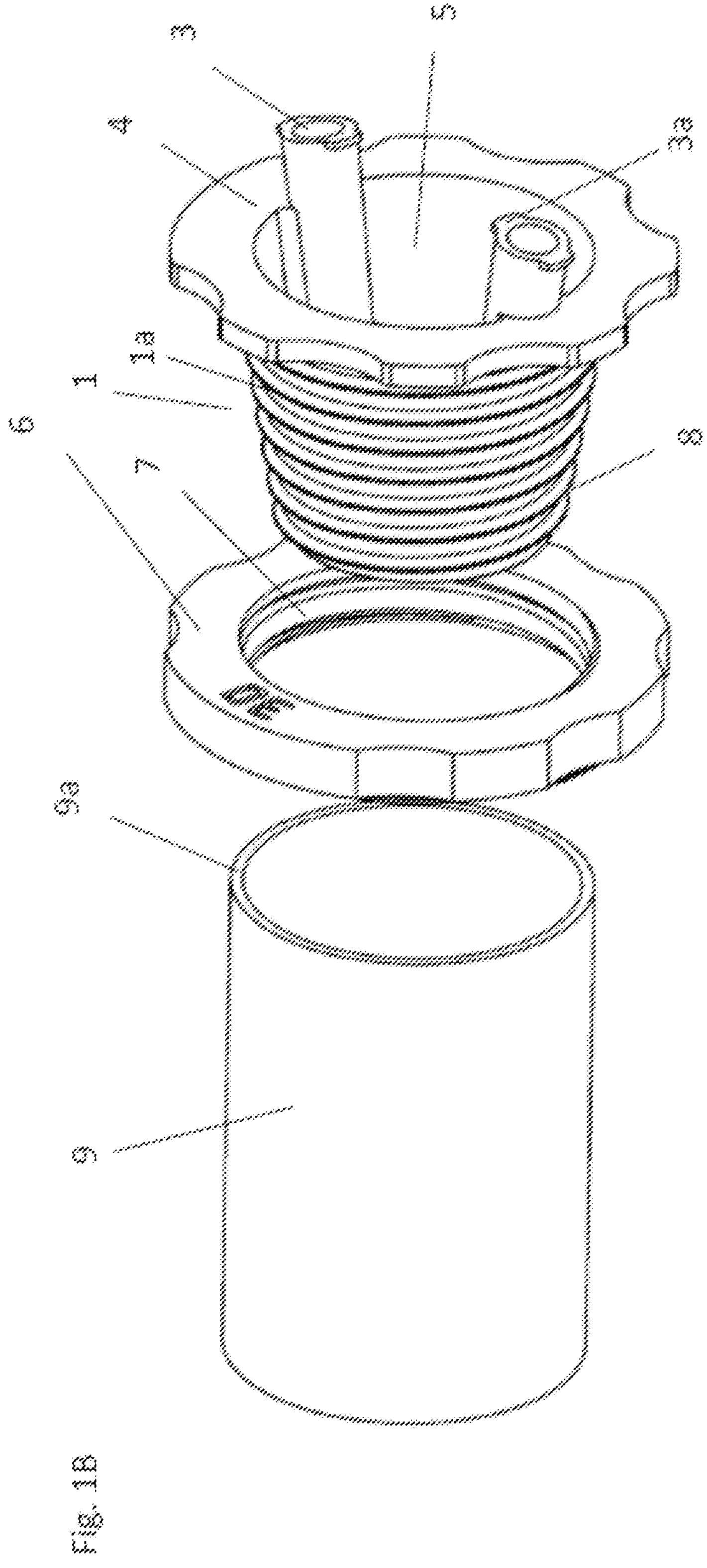
FIG. 1B shows an exploded perspective view of another exemplary single walled device.

FIG. 1B depicts another embodiment of an exemplary device, which is relatively similar to the exemplary device shown in FIG. 1A. However, one appreciable difference between the two devices is that the device of FIG. 1B is a single walled device, whereas the device of FIG. 1A has a double wall. A single walled device permits a simpler production and use of less material. Here, the backing portion and the connector portion are also formed integrally with an inner area of the connector portion forming the view port. Like the device shown in FIG. 1A, the connector portion of FIG. 1B also has an outer surface that comprises an external thread, and a pair of fluid conduits formed as tubular structures extending from the connector portion to the base and towards the graft. The device of FIG. 1B may also be secured to the distal end of the graft with a complementary second fastening element, shown again as a screw nut.

Figure 2A:
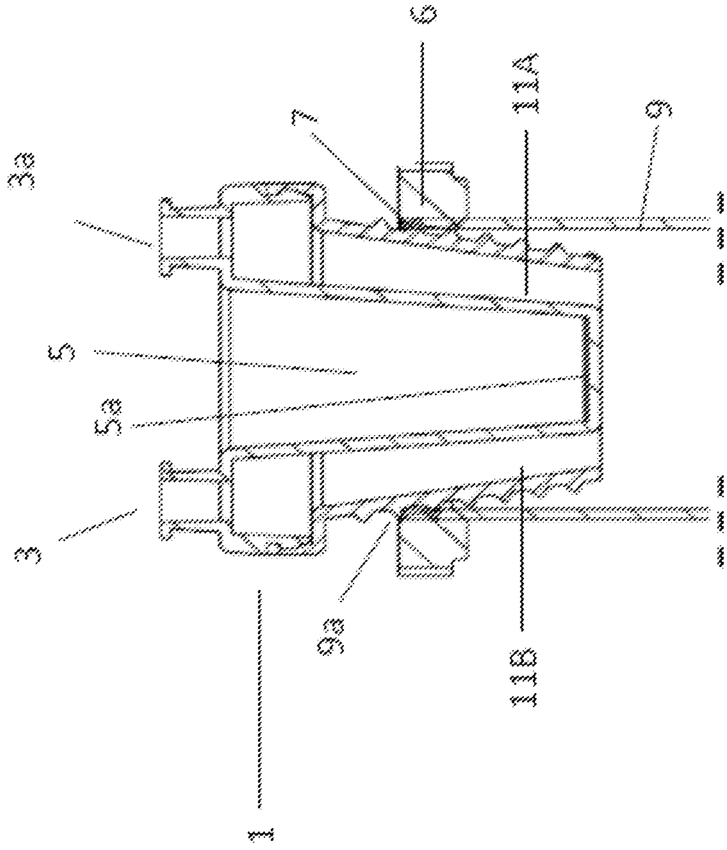
FIG. 2A shows a cross-sectional view of the device of FIG. 1A attached to a tubular vascular graft.
Figure 2B:
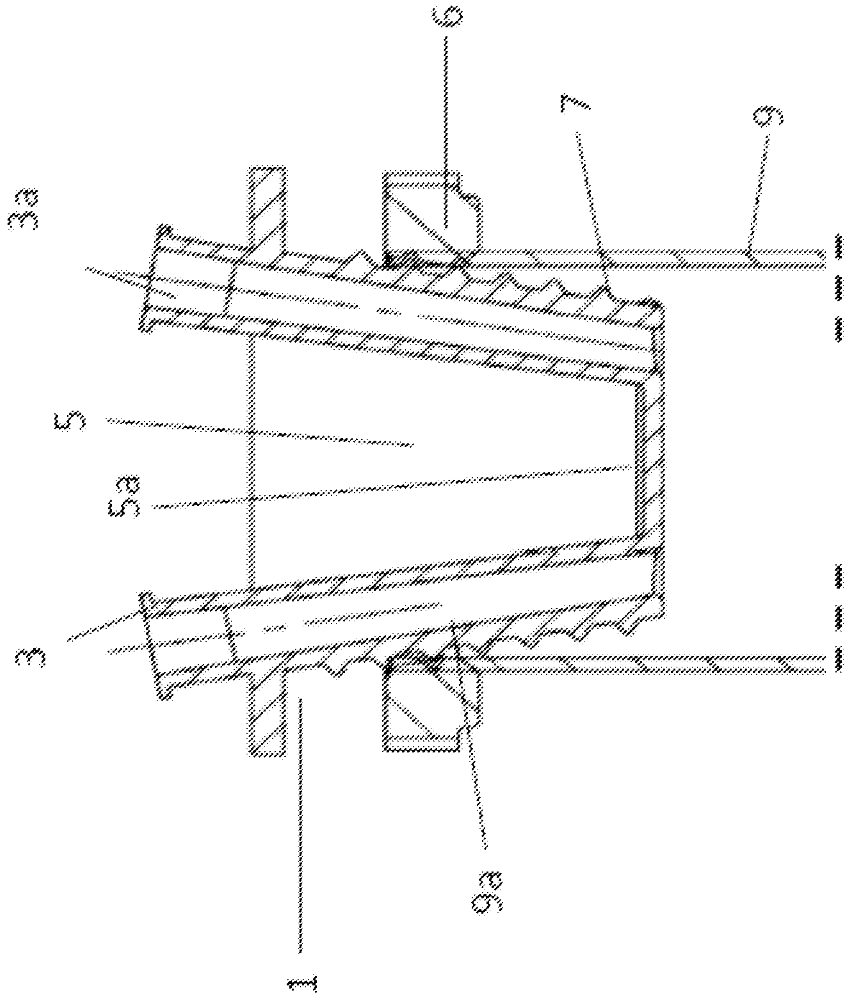
FIG. 2B shows a cross-sectional view of the device of FIG. 1B attached to a tubular vascular graft.

FIGS. 2A and 2B depict a cross-section of the devices of FIGS. 1A and 1*b*, respectively, when the devices are secured to a tubular vascular graft. Here, the distal end of the device has been inserted into an opening at the distal end of the graft. The tubular vascular graft is shown to be sealingly secured between the connector portion and the second fastening element. Additionally, formed in the backing portion and the connector portion is a chamber (11*a*, 11*b*). The chamber is formed between an inner wall and an outer wall of the device and is adapted to trap air bubbles introduced into the device during pressurization outside of view of the transparent window at the abutment (5*a*).

Figure 2C:
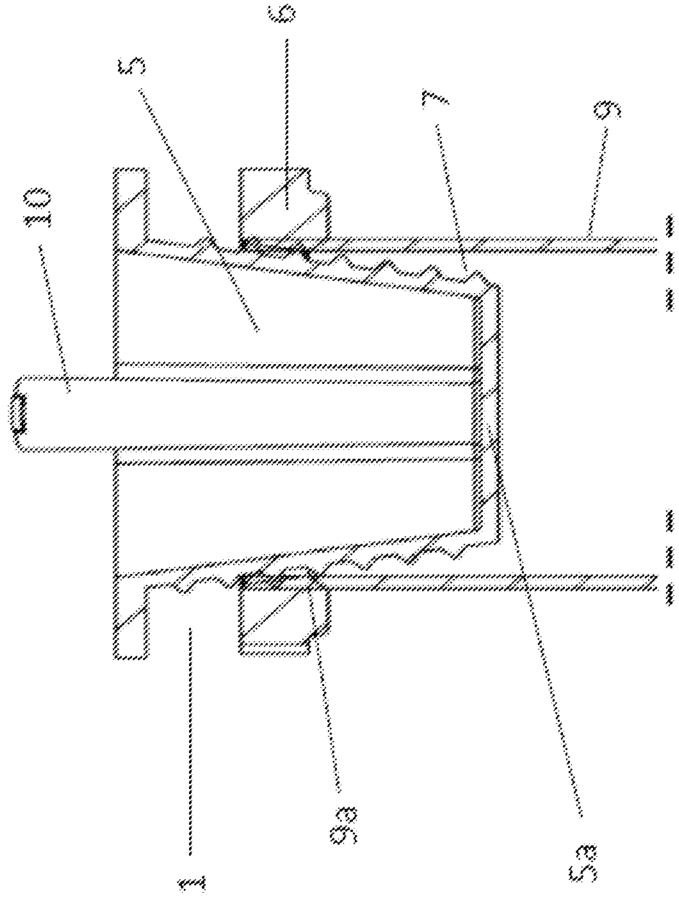
FIG. 2C shows another cross-sectional view of the device of along the line Y in FIG. 2B.

FIG. 2C depicts an alternative cross-section of the device of FIG. 1B. Here, a visualisation tool (10) is shown disposed in the view port and in contact with the abutment.

Figure 3:
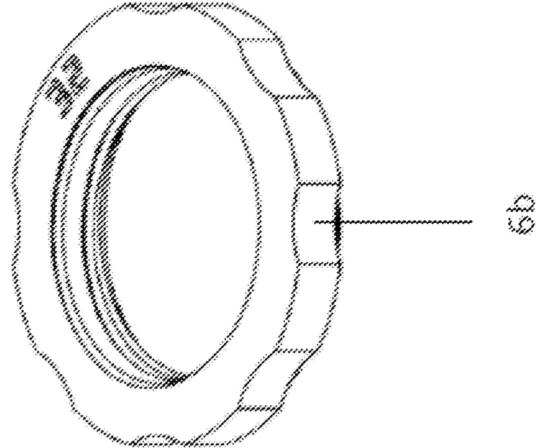
FIG. 3 shows a perspective view of a plurality of exemplary second fastening elements.
Figure 3:
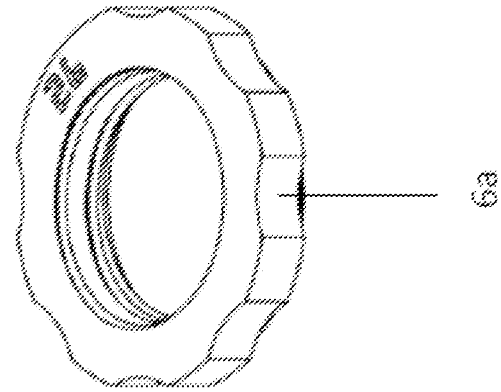

FIGS. 3A and 3B show two differently sized second fastening elements (6*a*, 6*b*). The second fastening elements are preferably coloured coded and/or numbered, and this indicates to which tubular vascular graft each should correspond in size.

These second fastening elements may be ideally provided as part of a system. Such a system includes the device, a plurality of differently sized tubular vascular grafts, and a plurality of differently sized second fastening elements, each second fastener element corresponding with a respectively sized tubular vascular graft and configured to be rotated onto the first fastening element for fitting engagement therewith. This system enables a surgeon to readily and quickly select, in real-time, an appropriately sized graft for an operation.

Figure 4A:
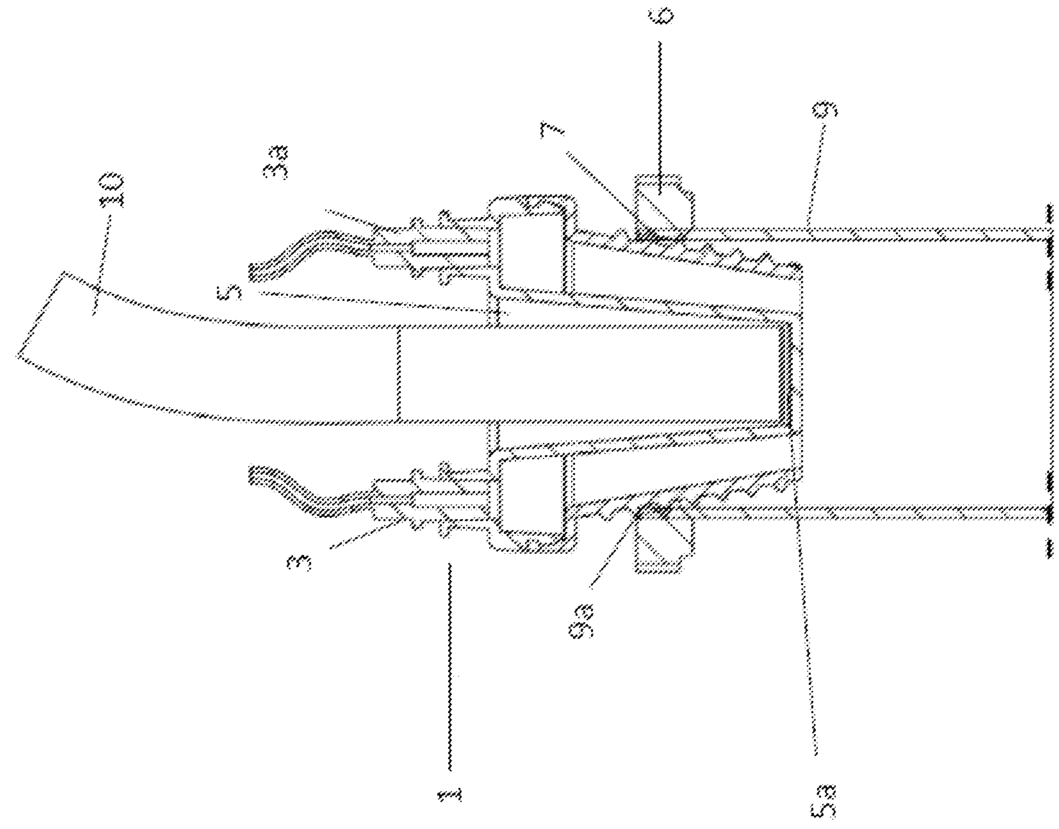
FIG. 4A shows a is a cross-sectional view of the device shown in FIG. 1A.
Figure 4B:
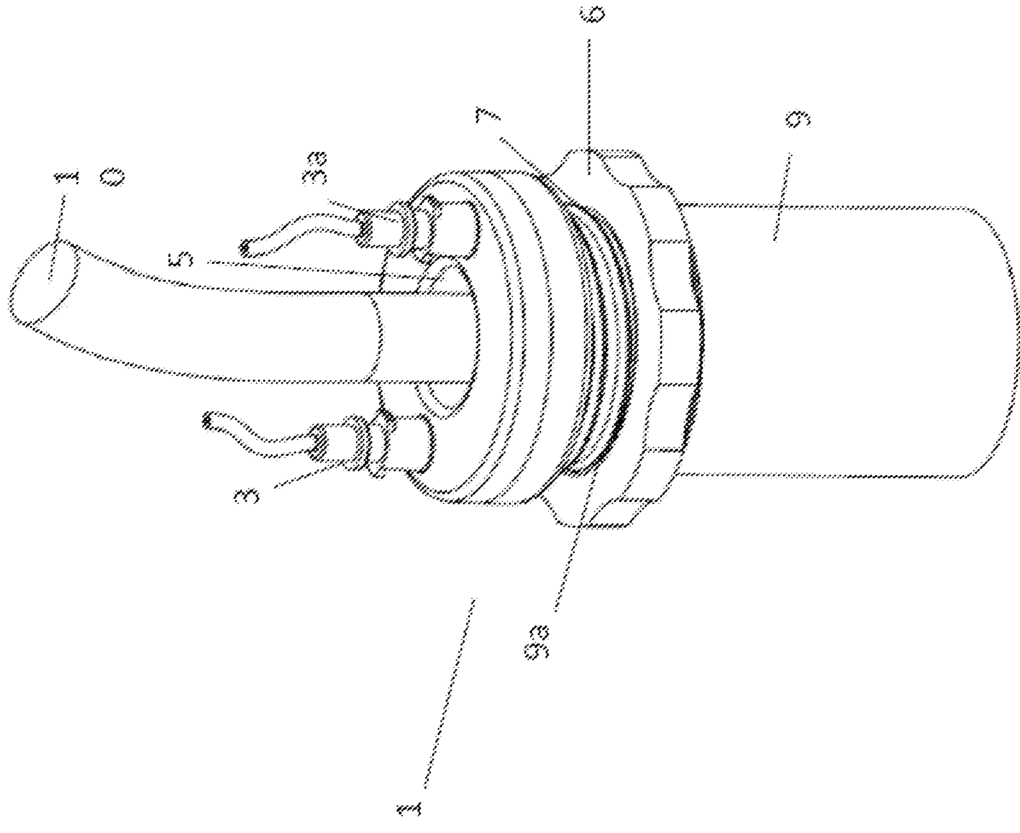
FIG. 4B shows a perspective view of the device shown in FIG. 4A in combination with a visualisation tool.

FIGS. 4A and 4B respectively depict a cross-sectional view and a perspective view of the device of FIGS. 1A and 2A, in combination with a visualisation tool (10), such as an endoscopic camera. Again, the visualisation tool (10) is inserted into the view port and extends all the way to the base where it contacts the abutment. FIG. 4A also shows the chamber (i.e., bubble trap cavity), which is the enclosed space between the inner and outer walls of the device and disposed below the fluid conduit elements (3, 3*a*). This chamber facilitates visualisation of the underlying operation site without having to remove all of the air entrapped in the lumen. Additionally, the device may comprise a hydrophilic material, either in at least the portion of the device (e.g., the view port) that is to come into contact with the introduced fluid, or in the form of a coating on one or more of the surface(s) of the device that is/are to come into contact with the introduced fluid.

Though not shown herein, it is further contemplated that the device may further comprise a light source. It is further envisioned that the light source may be integrated into the device, may be a standalone component that is temporary introduced into, for example, the view port, or may be an element integrated with or on another component, such a visualisation tool.

Figure 5A:
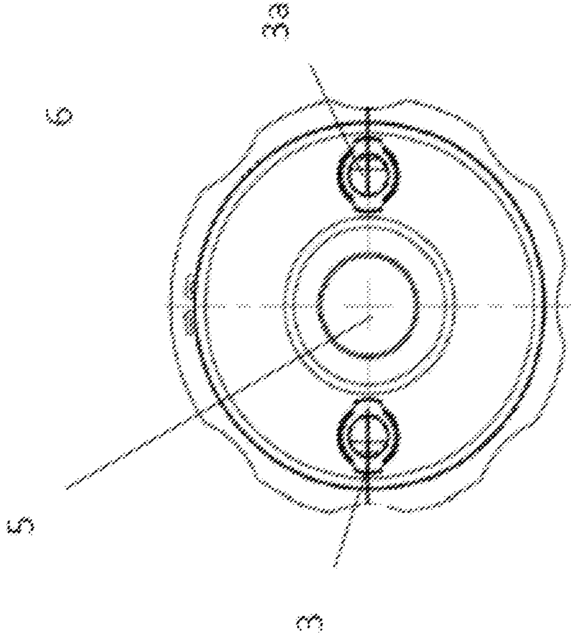
FIG. 5A shows a top-down schematic view of the device shown in FIG. 1A.
Figure 5B:
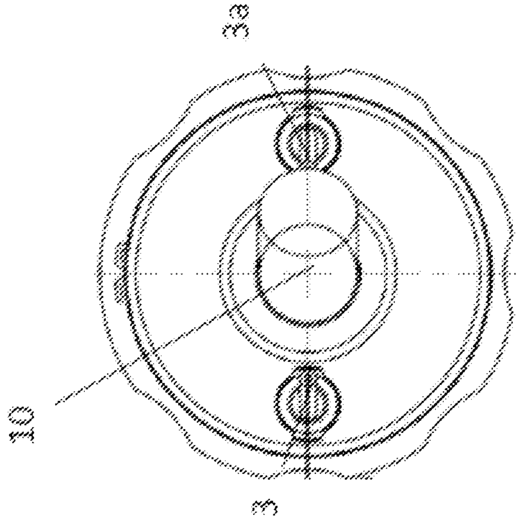
FIG. 5B shows a top-down schematic view of the device shown in FIG. 1A in combination with a visualisation tool.
Figure 5C:
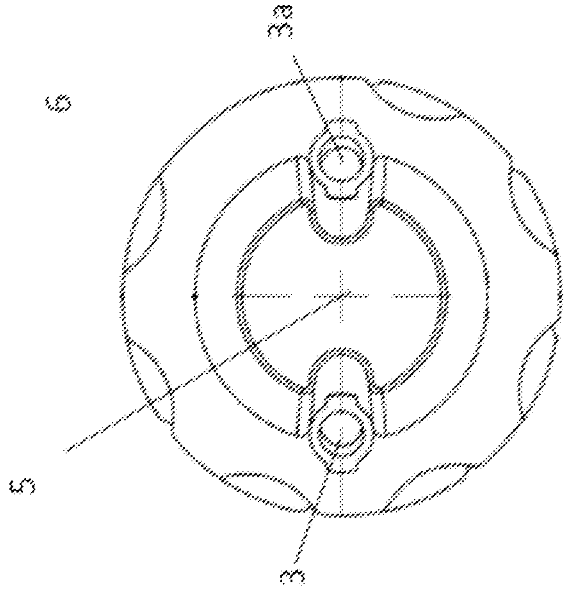
FIG. 5C shows a top-down schematic view of the device shown in FIG. 1B.

Further, FIGS. 5A to 5C each depict a top view of one of the exemplary devices shown in FIGS. 1A and 1B. More specifically, FIG. 5A shows the device of FIG. 1A with an open view port; in other words, no additional element or tool is provided in the view port. FIG. 5B shows the device of FIG. 1A with a visualisation tool disposed in the view port. Finally, FIG. 5C, shows the device of FIG. 1B with an open view port without any additional element or tool provided therein. While the invention has been described herein by reference to certain embodiments, it is to be understood that modification in addition to those described herein may be made to the structure(s) and the techniques described herein without departing from the spirit and scope of the invention. Accordingly, although specific embodiments have been described, they are only examples and are not limiting upon the scope of the invention.

The invention claimed is:

1. A device for simultaneous intraoperative leak testing and visualisation of a heart valve seat or functioning during a valve-sparing aortic root replacement, aortic valve repair, supracoronary ascending aortic replacement, pulmonary autograft, or any other operation leading to valve incompetence, the device comprising:

an end cap configured to engage with and to sealingly close an opening of a tubular vascular graft or native aorta, the end cap comprising an interior, an exterior, a backing portion, a connector portion arranged adjacent to the backing portion, a view port arranged in the backing portion and protruding along a central axis from the backing portion through at least a part of the connector portion, and at least one fluid conduit element adapted to provide fluid communication between the interior and the exterior, the connector portion comprising a body with opposing proximal and distal ends, the distal end dimensioned for placement inside of the opening of the tubular vascular graft, a first fastening element provided on an outer circumference of at least the distal end of the body of the connector portion, the first fastening element comprising an external thread, wherein the external thread comprises a thread pitch, the thread pitch sized such that the first fastening element can fittingly engage with the tubular vascular graft, wherein the external thread pitch is configured to engage with a second fastening element comprising a through hole with an inner circumference, the inner circumference comprising an internal thread, the second fastening element configured to be rotated onto the first fastening element for fitting engagement therewith, and wherein the external thread of the first fastening element is configured to sealingly secure the graft between the first and second fastening element by less than one rotation of the second fastening element around the outer circumference, and whereby the fitting engagement provides a fluid and pressure tight seal around the tubular vascular graft.

2. The device according to claim 1, wherein the connector portion is formed as a hollow cylindrical, conical, frusto-conical, stepped conical, stepped cylindrical, or tapered body for engaging with an interior of a distal end of the tubular vascular graft.

3. The device according to claim 1, wherein a shape of the connector body is dimensioned to engage with different grafts having different inner diameters.

4. The device according to claim 1, wherein the device has an essentially, axially symmetric form.

5. The device according to claim 1, wherein the external thread comprises a rounded edge.

6. The device according to claim 1, wherein the backing portion and the connector portion are either formed integrally or from two elements configured to fit and mutually engage to form a double walled chamber and/or wherein the backing portion and connector portion form a chamber adapted to collate entrapped air bubbles outside of view of the view port, and preferably comprise a hydrophilic material.

7. The device according to claim 1, wherein the view port comprises an insertion opening sized to receive a visualisation tool for visualisation of the heart valve seat under a fluid pressure differential, the view port preferably formed as a tapered conical protrusion in the backing portion extending toward the connector portion to permit an angle of the visualisation tool relative to a viewing position to be adjusted while the device is maintained in position, and preferably spaced in an axial direction from the backing portion toward a lumen of the tubular vascular graft.

8. The device according to claim 7, wherein the view port further comprises an inner engagement means for the visualisation tool, the inner engagement means extending centrally through the device in a longitudinal direction and ending at the backing portion, and wherein the visualisation tool is preferably an endoscopic camera.

9. The device according to claim 1, wherein the view port comprises a transparent window element as a closure abutment to sealingly close the view port towards a lumen of the tubular vascular graft and/or wherein the view port further comprises a seal, preferably a sheath or an O-ring adapted to engage with one or more of a visualisation tool and an illumination tool.

10. The device according to claim 1, wherein the view port is adapted to be filled with a fluid into which a visualisation tool is immersed.

11. The device according to claim 1, comprising a transparent material, the device preferably formed in one or more essentially transparent polymeric parts, and preferably by injection moulding.

12. The device according to claim 1, wherein the at least one fluid conduit element comprises a standardized, pressure-proof fluid connector that is preferably a Luer connector.

13. The device according to claim 1, further comprising one or more further fluid conduits, each further fluid conduit preferably comprising a standardized, pressure-proof fluid connector.

14. The device according to claim 1, wherein the end cap further comprises at least one of:

a) an inner wall, an outer wall, and an interior space therebetween configured to trap air bubbles outside of view of the view port, and preferably a hydrophilic material; and b) a light source that is preferably built-in or integrated into a portion of the end cap.

15. The device according to claim 1, wherein the second fastener element comprises a circular fastening body that is preferably a screw nut.

16. A system for simultaneous intraoperative leak testing and visualisation of a heart valve seat or functioning during a valve-sparing aortic root replacement, aortic valve repair, supracoronary ascending aortic replacement, pulmonary autograft, or any other operation involving valve incompetence, the system comprising:

the device according to claim 1, a plurality of differently sized tubular vascular grafts, and a plurality of differently sized second fastening elements, each second fastening element corresponding with a respectively sized tubular vascular graft and configured to be rotated onto the first fastening element for fitting engagement therewith, wherein each differently sized tubular vascular graft is sealingly securable between the first fastening element and the respectively sized second fastening element by less than one rotation of the respectively sized second fastening element around the outer circumference of the first fastening element.

17. The system according to claim 16, further comprising a fluid reservoir comprising a means to measure at least one of volume of fluid flow over time and pressure applied.

18. The system according to claim 17, wherein the fluid reservoir comprises a metered pump unit, which is preferably part of a heart lung machine comprising a flow meter.

19. A method for visualising an aortic root segment of an ascending aorta in a patient during a valve-sparing surgery using the device according to claim 1, the method comprising the steps of:

a) providing a tubular vascular graft corresponding in size to a diameter of an aortic valve-to-be-spared or an aortic root, the tubular vascular graft having opposing proximal and distal ends and a lumen, b) attaching the proximal end of the tubular vascular graft to the aortic valve-to-be-spared using one or more of a hook, a barb, an adhesive material, a staple, and a suture, c) sealingly attaching the device to the distal end of the tubular vascular graft, d) connecting the device to a fluid reservoir, preferably a metered pump unit, e) filling the lumen with a fluid to test relative fluid-tightness of the tubular vascular graft and/or to measure the fluid flow over time, and f) inserting a visualisation tool into the interior of the end cap to visualise the aortic heart valve seat under fluid pressure.

20. The device of claim 1, wherein the external and internal threads each comprise a respective thread pitch, the respective thread pitches sized such that the first and second fastening elements are fittingly engaged with the tubular vascular graft sealingly secured therebetween by less than one rotation of the second fastening element around the outer circumference, and whereby the fitting engagement provides a fluid and pressure tight seal around the tubular vascular graft.

* * * * *